United States Patent [19]

Katz et al.

[11] Patent Number: 5,073,365

[45] Date of Patent: Dec. 17, 1991

[54] CLINICAL AND PERSONAL CARE ARTICLES ENHANCED BY LUBRICANTS AND ADJUVANTS

[75] Inventors: Martin Katz, Menlo Park; Helen C. Leong, Atherton; Chung-Heng Cheng, San Jose, all of Calif.

[73] Assignee: Advanced Polymer Systems, Redwood City, Calif.

[21] Appl. No.: 359,546

[22] Filed: Jun. 1, 1989

[51] Int. Cl.⁵ .................... A61F 13/28; A61K 9/14; A61M 25/00

[52] U.S. Cl. .................... 424/489; 424/484; 424/501; 427/2; 514/951; 604/12; 604/265; 604/363

[58] Field of Search ............ 424/489, 484, 501, 419, 424/81; 514/963, 951; 604/265, 292, 12, 363; 427/2; 252/11

[56] References Cited

U.S. PATENT DOCUMENTS

| | | | |
|---|---|---|---|
| 3,294,726 | 12/1966 | Wyner | 427/2 |
| 3,896,807 | 7/1975 | Buchalter | 604/292 |
| 4,053,379 | 10/1977 | Fox et al. | 427/36 |
| 4,068,757 | 1/1978 | Casey | 604/292 |
| 4,143,423 | 3/1979 | Sternlieb | 427/2 |
| 4,540,407 | 12/1966 | Dunn | 604/292 |
| 4,592,920 | 6/1986 | Murtfeldt | 427/2 |
| 4,690,825 | 9/1987 | Won | 424/501 |
| 4,882,204 | 11/1989 | Tenenbaum | 427/421 |

*Primary Examiner*—Jeffrey E. Russel
*Attorney, Agent, or Firm*—Townsend and Townsend

[57] ABSTRACT

Articles for use in contact with animal tissue, such as surgical and first aid supplies, health care products and personal hygiene products, are dusted with microspheres for lubricating purposes or for the application of diffusible adjuvants. In the latter case, the microspheres are porous, with a continuous network of pores open to the exterior of the particles, permitting outward diffusion of the adjuvants at a controlled rate depending on pore size. The adjuvants include such substances as biologically active substances, deodorants, flavors, fragrances, and liquid lubricants.

18 Claims, No Drawings

CLINICAL AND PERSONAL CARE ARTICLES ENHANCED BY LUBRICANTS AND ADJUVANTS

BACKGROUND OF THE INVENTION

This invention relates to surgical supplies, health care products, personal hygiene products, and clinical and personal care articles in general. In particular, this invention is directed to devices used in contact with animal, particularly human tissue, including both external and internal tissues, such as dermal tissues, mucus membranes and others. This invention is of particular interest with regard to devices made of natural or synthetic rubbers such as, for example, polyisoprenes, polyurethanes, vinyl plastisols, acrylic polyesters, polyvinylpyrrolidone-polyurethane interpolymers, butadiene rubbers, styrene-butadiene rubbers, acrylate-butadiene rubbers, acrylonitrile-butadiene rubbers, chloroprene rubbers, and rubber latices, in any form which will benefit in use from an additive applied in unbonded manner as a surface coating.

Additives which serve as lubricants are useful for a variety of purposes. On devices such as catheters, condoms, vaginal diaphragms, tampons, ostomy products, prosthetic devices, sponges, cervical caps, and tubing in general, lubricants serve to aid insertion. On devices worn externally such as rubber or plastic sheets, diapers and garments, lubricants enhance comfort to the skin. On surgical rubber gloves, lubricants enhance the ease of use, both inside and outside. Conventional dry lubricants such as talcum and other lubricating powders have a layer-lattice or plate-like structure and entail some friction in use. Many such powders also cause allergic reactions. In most cases, they cannot be used on open wounds since they cause infection. Wet lubricants are problematic since they are difficult to disperse over a wide area in small amounts. In addition, some wet lubricants are physically or chemically incompatible with the substrate by virtue, for example, of their being non-wetting of the substrate surface, or reactive with the substrate (mineral oil, for example, is reactive toward certain natural and synthetic rubbers).

Adjuvants other than lubricants include a wide range of biologically active substances, chemically active substances, and substances supplying their own inherent character to the substrate. These are applicable to devices for surgical use, first aid use, birth control use and personal hygiene use, including those devices listed in the preceding paragraph. Examples of such adjuvants are antiseptics, germicides, antimicrobials, antifungals, anti-infectives, anti-viral agents, anesthetics, spermicides, astringents, coagulants, anticoagulants, deodorants, emollients, moisturizers, astringents, flavors and fragrances. The disadvantage of applying these substances in full strength to the substrate is a high initial effect, followed by a rapid decrease as diffusion to or loss to contacting membranes or tissues occurs, plus instability in some cases due to exposure to the atmosphere. The decline in effectiveness is similar in general to a first order chemical reaction.

SUMMARY OF THE INVENTION

In one aspect of the invention, lubrication is achieved by dusting the surface of the article with a lubricant powder comprised of substantially spherical, microscopic particles of a chemically and biologically inert solid.

In a second aspect of the invention, adjuvants including lubricants and active substances such as those mentioned above are applied to the article by dusting its surface with microscopic porous particles of an inert solid material with the adjuvants retained inside the pores by capillary forces, the adjuvants being in a form in which they can diffuse outward when the article is in use. The pores are interconnected and open to the particle surface, permitting full diffusion outward of the adjuvant.

The solid particles themselves include certain types which are common to both aspects of the invention, notably those which are porous and substantially spherical.

In accordance with the second aspect of the invention, the retained adjuvant may either be in liquid or solid form, the liquids including species which are liquid at ambient conditions as well as solid species dissolved in suitable solvents. These liquids diffuse out of the pores upon rubbing contact or contact with the natural bodily secretions present on the tissues with which the device or article is placed in contact, in accordance with known principles of the diffusion of one liquid through another. Adjuvants in solid form are delivered to the contacted area by gradually dissolving into the bodily secretions at the points of exposure through the pore openings at the particle surfaces. Once dissolved, the adjuvants diffuse in the same manner as those which are normally liquid.

The particles function as controlled delivery systems for the retained adjuvants, providing a wide range of advantages over the conventional formulations. Release of the adjuvants from the pores occurs in sustained manner, providing a continuous fresh supply to the tissues or areas with which the article is brought into contact. The activity-time curve of the adjuvant is thus extended and flattened out. The magnitude of the release rate is controlled by the pore volume distribution in the particle itself, notably the total pore volume and the average pore diameter. Selection of the values of these parameters according to predetermined standards provides control of the release rate to desired levels. A further advantage is the ability of the system to withstand a higher concentration of adjuvant both inside the pores themselves and at any localized area without the magnitude of side effects previously experienced at these levels. A still further advantage is the ability of the system to spread a low amount of the adjuvant over a broad area in substantially uniform manner, thereby avoiding waste and further controlling the adjuvant's activity level.

The volume of adjuvant retained in the pores awaiting diffusion is held in reserve with minimal exposure to the atmosphere. For those adjuvants which are volatile and produce irritating vapors, this retention in the pores reduces the rate of volatilization. At the same time, the amounts held in reserve are held out of contact with the tissues until their release, thus lessening any high initial effect and preventing undesirable reactions of the tissues to high concentrations.

As will be seen from the description which follows, the present invention is applicable to a wide range of adjuvants, and the degree of control which the system imparts to the various properties of the formulation and its use provide adjuvants with a wide range of utility with enhanced safety and effectiveness.

DETAILED DESCRIPTION OF THE INVENTION AND PREFERRED EMBODIMENTS

The beads or microspheres used in connection with preferred embodiments of the present invention are rigid, open-pore, chemically and biologically inert particles. The pores are interconnected and open to the particle surface to an extent that substantially full communication is provided between the internal pore space and the exterior of the particle.

In their most convenient form, the particles are generally spherical in shape, due to the use of suspension polymerization as a preferred method of preparation. While the microspheres may vary widely in size, those falling within the range of about one to about 100 microns in diameter, preferably from about 10 to about 40 microns, will provide the best results. Microspheres within these size ranges are appealing from an aesthetic point of view by imparting a smooth feel to the touch.

The pore dimensions within the spheres may also vary widely, with optimum dimensions depending on the chemical characteristics of the polymers used as well as the diffusive characteristics of the adjuvant retained inside. Different systems will thus call for different optimum ranges of pore volume distribution to obtain the most desirable properties for the overall formulation. In general, however, best results are obtained with total pore volumes ranging from about 0.01 to about 4.0 cc/g. preferably from about 0.1 to about 2.0: surface areas ranging from about 1 to about 500 m$^2$/g. preferably from about 20 to about 200: and average pore diameters ranging from about 0.001 to about 3.0 micron, preferably from about 0.003 to about 1.0 micron. Following conventional methods of measuring and expressing pore sizes, the pore diameters are measured by techniques such as nitrogen adsorption isotherms or mercury intrusion and are based on the model of a pore of cylindrical shape.

The microspheres are conveniently formed by suspension polymerization in a liquid-liquid system. In general a solution containing monomers and a polymerization catalyst (if used) is formed which is immiscible with water. When porous microspheres are desired, an inert liquid fully miscible with the solution but immiscible with water is included in the solution. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting rigid beads are recovered from the suspension. If the inert liquid has been included, the beads are solid porous structures, the polymer having formed around the inert liquid, thereby forming the pore network. The liquid has accordingly served as a porogen, or pore-forming agent, and occupies the pores of the formed beads.

In certain cases, the adjuvant itself may serve as the porogen, in which case the porous beads recovered from the suspension immediately after polymerization are substantially ready for use, following removal of surface moisture, and any further processing steps of this nature. In these cases, microsphere formation and incorporation of the adjuvant are performed in a single step. This may accordingly be termed a one-step procedure. Adjuvants which can be used in this manner are those which meet the following criteria:

1. They are either fully miscible with the monomer mixture or capable of being made fully miscible by the addition of a minor amount of non-water-miscible solvent;
2. They are immiscible with water, or at most only slightly soluble; and
3. They are inert with respect to the monomers, and stable when in contact with any polymerization catalyst used and when subjected to any conditions needed to induce polymerization (such as temperature and radiation).

For adjuvants which do not meet these criteria, their placement inside the pores may be achieved by impregnation of preformed dry porous polymer beads. The product is thus prepared in two steps performed in sequence, the polymerization being performed first with a substitute porogen which is then removed and replaced by the adjuvant. Materials suitable as substitute porogens will be liquid substances which meet the above criteria and which have the further characteristic of being readily extracted from the pore network of the beads once polymerization is complete. This covers a wide range of substances, notably inert, nonpolar organic solvents. Some of the most convenient examples are alkanes, cycloalkanes, and aromatics. Examples of such solvents are alkanes of 5 to 12 carbon atoms, straight or branched chain, cycloalkanes of 5 to 8 carbon atoms, benzene, and alkyl-substituted benzenes such as toluene and the xylenes. Porogens of other types include $C_{12}$–$C_{15}$ alcohols benzoate, perfluoro polyethers, and silicone oils. Examples of silicone oils are polydimethylcyclosiloxane, hexamethyldisiloxane, cyclomethicone, dimethicone, amodimethicone, trimethylsilylamodimethicone, polysiloxane-polyalkyl copolymers (such as stearyl dimethicone and cetyl dimethicone), dialkoxydimethylpolysiloxanes (such as stearoxy dimethicone), polyquaternium 21, dimethicone propyl PG-Betaine, dimethicone copolyol and cetyl dimethicone copolyol.

Once polymerization is complete, the porogen may be removed by solvent extraction, evaporation, or similar conventional operations.

A further advantage of the use of this two-step process is that it permits the removal of unwanted species from the polymerized structures prior to impregnation with the adjuvants. Examples of unwanted species include unreacted monomers, residual catalyst, and surface active agents and/or dispersants remaining on the sphere surfaces. A further advantage of this technique is that it permits one to select the amount and type of porogen as a means of controlling the pore characteristics of the finished bead. One is thus no longer bound by the limitations of the adjuvant as they affect the structure of the bead itself. This also permits partial rather than full filling of the pores with adjuvant, and further control over pore size and distribution by selection among swelling and non-swelling porogens.

Extraction of the porogen and its replacement with (i.e., impregnation of the dry bead with) the adjuvant in the two-step procedure may be effected in a variety of ways, depending on the chemical nature of the porogen and its behavior in combination with that of the other species present. The beads are first recovered from the suspension by filtration, preferably using vacuum filtration apparatus (such as a Buechner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used—i.e., where the porogen, unreacted monomer and water will form an azeotrope. In these cases, steam distillation is an effective way of extracting porogen from the beads. This again may be followed by drying under vacuum.

Once the beads are rendered dry and free of the substitute porogen and any unwanted organic materials, they are impregnated with the adjuvant according to conventional techniques. The most convenient such technique is contact absorption, aided by solvents if necessary to enhance the absorption rate.

The following is a nonexhaustive list of examples of adjuvants which may be used in accordance with the present invention:
anti-infectives
bacitracin, neomycin, polymyxin B, tetracyclines, benzoic acid, salicylic acid, candicidin, nystatin, zincundecate, benzene hexachloride (gamma), benzyl benzoate, benzalkonium chloride, hexachlorophene, iodine, iodochlorhydroxyquin, nonoxynol 9.
anti-inflammatory agents
hydrocortisone, betamethasone valerate, fluocinolide, fluocinolone acetonide, triamcinolone acetonide.
antipruritics and local anesthetics
benzocaine, camphor, phenol, menthol, dimethisoquin hydrochloride, pramoxine hydrochloride.
antihistaminics
diphenhydramine hydrochloride, mepyramine maleate, promethazine
astringents
acetic acid, aluminum subacetate, silver nitrate, tannic acid .
anti-hidrotics
aluminum chlorhydroxide, formalin, anticholinergics.
keratolytic agents and caustics
resorcinol, salicylic acid, silver nitrate, sulfur.
keratoplastic agents
coal tar, urea, vitamin A.
Of the antiseptics in the above list, one of particular interest is nonoxynol 9, which is a poly(ethylene glycol) p-nonylphenyl ether of the formula

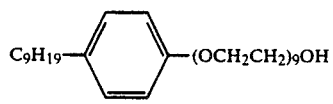

which has utility as an antiseptic, spermicide and antiviral agent, and as such is particularly useful for prophylaxis and may be applied to beads dusted over condoms, diaphragms, contraceptive sponges and similar articles to prevent the transmission of venereal diseases, possibly including AIDS.

Adjuvants which are solid at ambient conditions may be first melted by heating, then held in the molten state during the contact absorption. Once impregnation has occurred, the particles may be cooled to ambient temperature and the molten adjuvants thus returned to solid form.

Certain adjuvants may also be combined in a eutectic mixture to produce a low-melting composition usable in a manner similar to that of a melt. Melts and eutectics in general may be used in either the one-step or two-step procedure.

The polymerization process and the various parameters and process conditions involved can be selected and adjusted as a means of controlling the pore characteristics and consequently the capacity and release characteristics of the ultimate product. For example, proper selection of the cross-linking means, the amount and type of cross-linking agent, and the amount and type of porogen are means of attaining such control. Certain polymerization conditions may also be varied to such effect, including temperature, degree of radiation where used, degree of agitation and any other factors affecting the rate of the polymerization reaction.

Cross-linking in the polymer formation is a major means of pore size control. Monomers which may be polymerized to produce cross-linked polymer beads in accordance with the present invention include polyethylenically unsaturated monomers, i.e., those having at least two sites of unsaturation, and monoethylenically unsaturated monomers in combination with one or more polyethylenically unsaturated monomers. In the latter case, the precentage of cross-linking may be controlled by balancing the relative amounts of monoethylenically unsaturated monomer and polyethylenically unsaturated monomer.

Monoethylenically unsaturated monomers suitable for preparing polymer beads for the polymer delivery system include ethylene, propylene, isobutylene, diisobutylene, styrene, ethylvinylbenzene, vinyltoluene, and dicyclopentadiene, esters of acrylic and methacrylic acid, including the methyl ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone: vinyl ethers, including vinyl methyl ether, vinyl ethyl ether, vinyl propyl ether, and vinyl isobutyl ether: and the like.

Polyethylenically unsaturated monomers which ordinarily act as though they have only one unsaturated group, such as isopropene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone: polyvinyl and polyallyl ethers of ethylene glycol, of glycerol, of pentaerythritol, of diethyleneglycol, of monothio- and dithio-derivatives of glycols, and of resorcinol: divinylketone, divinylsulfide, allyl acrylate, diallyl maleate, diallyl fumarate diallyl succinate, diallyl carbonate, diallyl malonate, diallyl oxalate, diallyl adipate, diallyl sebacate, divinyl sebacate, diallyl tartrate, diallyl suilicate, triallyl tricarballylate, triallyl aconitate, triallyl citrate, triallyl phosphate, divinyl naphthalene divinylbenzene, trivinylbenzene alkyldivinylbenzenes having from 1 to 4 alkyl groups of 1 to 2 carbon atoms substituted on the benzene nucleus alkyltrivinylbenzenes having 1 to 3 alkyl groups of 1 to 2 carbon atoms substituted on the benzene nucleus: trivinylnaphthalenes, and polyvinylanthracenes.

Particularly preferred polymer delivery systems of the present invention are formed by the copolymerization of styrene and divinylbenzene, vinyl stearate and divinylbenzene, or methylmethacrylate and ethylene glycol dimethylmethacrylate. Usually, the monoethylenically unsaturated monomer will be present at from about 20% to 80% of the monomer mixture, with the polyethylenically unsaturated monomer forming the remainder of the mixture. Particularly preferred is the styrene-divinylbenzene polymeric bead which consists essentially of a hydrocarbon backbone with benzene rings and which is substantially completely free from reactive groups.

Examples of organic solvents in which such substances can be dissolved to facilitate absorption include liquid petrolatum, petroleum ether, ethanol, higher alcohols, isopropyl myristate, diisopropyl adipate and mineral oil. The solvent can then be evaporated or, if desired, retained together with the absorbed substance within the pores. Other formulating materials, such as carriers or adjuvants and the like can also be present, and will be incorporated into and onto the beads together with the adjuvants of interest and any other materials present.

The adjuvant should comprise between approximately 5% and approximately 65% of the total weight of the impregnated beads.

The foregoing description is directed primarily to preferred embodiments and practices of the present invention. It will be readily apparent to those skilled in the art that further changes and modifications in the actual implementation of the concepts described herein can be made without departing from the spirit and scope of the invention as defined by the following claims.

What is claimed is:

1. A method of applying a liquid substance to the surface of an article to be used in contact with tissue, comprising dusting said surface with solid particles substantially spherical in shape with an average diameter of from about one micron to about 100 microns and containing a substantially continuous network of pores open to the exterior of said particles, with said liquid substance residing in said pores.

2. A method in accordance with claim 1 in which said liquid substance is a member selected from the group consisting of lubricants, flavor-bearing liquids, fragrance-bearing liquids, and biologically active liquids.

3. A method in accordance with claim 1 in which said liquid substance is a lubricant.

4. A method in accordance with claim 1 in which said article is made of rubber, and said liquid substance is mineral oil.

5. A method in accordance with claim 1 in which said liquid substance is a biologically active liquid.

6. A method in accordance with claim 5 in which said biologically active liquid is a member selected from the group consisting of antiseptics, antibiotics, antifungals, anti-infectives, anesthetics and spermicides.

7. A method in accordance with claim 1 in which said solid particles are substantially spherical in shape and have an average diameter of about 10 microns to about 40 microns.

8. A method in accordance with claim 7 in which said solid particles have a total pore volume of about 0.01 cc/g to about 4.0 cc/g.

9. A method in accordance with claim 7 in which said solid particles have a total pore volume of about 0.1 cc/g to about 2.0 cc/g.

10. A method in accordance with claim 7 in which said solid particles have a surface area of about about 500 $m^2/g$.

11. A method in accordance with claim 7 in which said solid particles have a surface area of about 20 $m^2/g$ to about 200 $m^2/g$.

12. A method in accordance with claim 7 in which said solid particles have an average pore diameter of about 0.001 micron to about 3.0 microns.

13. A method in accordance with claim 7 in which said solid particles have an average pore diameter of about 0.003 microns to about 1.0 micron.

14. A method in accordance with claim 1 in which said solid particles are formed of a cross-linked polymer.

15. A method in accordance with claim 14 in which said cross-linked polymer is a copolymer of styrene and divinylbenzene.

16. A method in accordance with claim 14 in which said cross-linked polymer is a copolymer of methyl methacrylate and ethylene glycol dimethacrylate.

17. A method in accordance with claim 1 in which said liquid substance comprises about 5% to about 65% of the weight of said solid particles with said liquid substance residing therein.

18. A method in accordance with claim 1 in which said article is a member selected from the group consisting of catheters, condoms, vaginal diaphragms, tampons, ostomy products, prosthetic devices, sponges, cervical caps, sheets, diapers, garments and surgical gloves.

* * * * *